United States Patent
Blattman et al.

(10) Patent No.: US 11,208,681 B2
(45) Date of Patent: Dec. 28, 2021

(54) HIGH THROUGHPUT OIL-EMULSION SYNTHESIS OF BOWTIE BARCODES FOR PAIRED MRNA CAPTURE AND SEQUENCING FROM INDIVIDUAL CELLS

(71) Applicant: ARIZONA BOARD OF REGENTS ON BEHALF OF ARIZONA STATE UNIVERSITY, Scottsdale, AZ (US)

(72) Inventors: Joseph Blattman, Scottsdale, AZ (US); Louis Schoettle, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/320,962

(22) PCT Filed: Aug. 14, 2017

(86) PCT No.: PCT/US2017/046794
§ 371 (c)(1),
(2) Date: Jan. 25, 2019

(87) PCT Pub. No.: WO2018/035055
PCT Pub. Date: Feb. 22, 2018

(65) Prior Publication Data
US 2019/0194724 A1    Jun. 27, 2019

Related U.S. Application Data (60) Provisional application No. 62/377,123, filed on Aug. 19, 2016.

(51) Int. Cl.
| | | |
|---|---|---|
| C12Q 1/68 | (2018.01) | |
| C12Q 1/6806 | (2018.01) | |
| C12Q 1/6869 | (2018.01) | |
| C12N 15/87 | (2006.01) | |

(52) U.S. Cl.
CPC .......... *C12Q 1/6806* (2013.01); *C12N 15/87* (2013.01); *C12Q 1/6869* (2013.01)

(58) Field of Classification Search
None
See application file for complete search history.

(56) References Cited

U.S. PATENT DOCUMENTS

| | | |
|---|---|---|
| 9,944,923 B2 | 4/2018 | Blattman |
| 2002/0190663 A1 | 12/2002 | Rasmussen |
| 2015/0292007 A1 | 10/2015 | Church |
| 2015/0315637 A1 | 11/2015 | Royyuru |
| 2016/0122752 A1 | 5/2016 | Blattman |
| 2018/0073014 A1 | 3/2018 | Emig |
| 2018/0216102 A1 | 8/2018 | Blattman |

FOREIGN PATENT DOCUMENTS

| | | |
|---|---|---|
| WO | 2012102616 | 8/2012 |
| WO | 2012106546 A2 | 8/2012 |
| WO | 2014200933 | 12/2014 |
| WO | 2018200884 A1 | 11/2018 |

OTHER PUBLICATIONS

Jabbari et al (ACS Combinatorial Science, 2015, vol. 17, pp. 535-547).*
Dekosky, B. J., et al. "Large-scale sequence and structural comparisons of human naive and antigen-experienced antibody repertoires." Proceedings of the National Academy of Sciences 113.19 (2016): E2636-E2645.
European Patent Office. Extended European Search Report for application 17841944.6. Dated Jan. 29, 2020.
IP Australia. Examination Report No. 1 for application 2017312947. Dated Jun. 29, 2020.
Japan Patent Office. Notification of Reasons for Refusal for application JP-A-2019-508961. Dated Mar. 24, 2020. With translation.
Korean Intellectual Property Office. Notice of Grounds for Refusal for application 10-2019-7007829. Dated May 21, 2020. With English Summary.
Rothemund, P.W., Folding DNA to create nanoscale shapes and patterns. Nature, 2006. 440(7082): p. 297-302.
Schietinger, A., et al., Rescued tolerant CD8 T cells are preprogrammed to reestablish the tolerant state. Science, 2012. 335(6069): p. 723-7.
Schoettle, Louis. Bowties, Barcodes, and DNA Origami: A Novel Approach for Paired-Chain Immune Receptor Repertoire Analysis. Arizona State University, 2017.
Seiler, P., et al., Enhanced virus clearance by early inducible lymphocytic choriomeningitis virus-neutralizing antibodies in immunoglobulin-transgenic mice. J Virol, 1998. 72(3): p. 2253-8.
Sharma, J., et al., Control of self-assembly of DNA tubules through integration of gold nanoparticles. Science, 2009. 323(5910): p. 112-6.
Sherwood AM, Desmarais C, Livingston RJ, Andriesen J, Haussler M, Carlson CS, Robins HS, Deep Sequencing of the Human TCR? and TCR Repertoires Suggests that TCRβ Rearranges After αβ and ?d T Cell Commitment, Sci Transl Med 3(90):90ra61.
Turner, S.J., et al., TCR alpha-chain usage can determine antigen-selected TCR beta-chain repertoire diversity. J Immunol, 1996. 157(11): p. 4979-85.
Tyagi, S. et al, Molecular beacons: probes that fluoresce upon hybridization. Nat Biotechnol, 1996. 14(3): p. 303-8.
Venturi, V., et al., Method for assessing the similarity between subsets of the T cell receptor repertoire. J Immunol Methods, 2008. 329(1-2): p. 67-80.
Venturi, V., et al., Methods for comparing the diversity of samples of the T cell receptor repertoire. J Immunol Methods, 2007. 321(1-2): p. 182-95.

(Continued)

*Primary Examiner* — Celine X Qian
(74) *Attorney, Agent, or Firm* — Quarles & Brady LLP (57) ABSTRACT

Methods for incorporation of unique bowtie-barcodes into a nucleic acid origami nanostructure (FIG. 1). In particular, provided herein are methods that facilitate pairing and analysis of nucleic acids from individual cells using, for example, high-throughput next-generation sequencing.

3 Claims, 7 Drawing Sheets

Specification includes a Sequence Listing.

(56) References Cited

OTHER PUBLICATIONS

Wei X, et al, Mapping the thermal behavior of DNA origami nanostructures, J Am Chem Soc 135(16):6165-76.
Williams, R., et al. Amplification of complex gene libraries by emulsion PCR. Nat Methods 3(7): 545-550.
Wu D, et al, High-Throughput Sequencing Detects Minimal Residual Disease in Acute T Lymphoblastic Leukemia, Sci Transl Med 4(134):134ra63.
Zhang, X., et al., Quantitative assessment of ratiometric bimolecular beacons as a tool for imaging single engineered RNA transcripts and measuring gene expression in living cells. Nucleic Acids Res, 2013. 41(15): p. e152.
Anoosha, P., et al., Discrimination of driver and passenger mutations in epidermal growth factor receptor in cancer. Mutat Res, 2015. 780: p. 24-34.
Arstila, T.P., et al., A direct estimate of the human alphabeta T cell receptor diversity. Science, 1999. 286(5441): p. 958-61.
Bartok, I., et al., T cell receptor CDR3 loops influence alphabeta pairing. Mol Immunol, 2010. 47(7-8): p. 1613-8.
Benenson, Y., et al., An autonomous molecular computer for logical control of gene expression. Nature, 2004. 429(6990): p. 423-9.
Blattman, J.N., et al., Evolution of the T cell repertoire during primary, memory, and recall responses to viral infection. J Immunol, 2000. 165(11): p. 6081-90.
Blattman, J.N., et al., Therapeutic use of IL-2 to enhance antiviral T-cell responses in vivo. Nat Med, 2003. 9(5): p. 540-7.
Bozic, I., et al., Accumulation of driver and passenger mutations during tumor progression. Proc Natl Acad Sci USA, 2010. 107(43): p. 18545-50.
Brandle, D., et al., T cell development and repertoire of mice expressing a single T cell receptor alpha chain. Eur J Immunol, 1995. 25(9): p. 2650-5.
Burns, R.P., Jr., et al., Molecular analysis of skewed Tcra-V gene use in T-cell receptor beta-chain transgenic mice. Immunogenetics, 1998. 47(2): p. 107-14.
Busse, C.E., et al., Single-cell based high-throughput sequencing of full-length immunoglobulin heavy and light chain genes. Eur J Immunol, 2014. 44(2): p. 597-603.
Cabaniols, J.P., et al., Most alpha/beta T cell receptor diversity is due to terminal deoxynucleotidyl transferase. J Exp Med, 2001. 194(9): p. 1385-90.
Casrouge, A., et al., Size estimate of the alpha beta TCR repertoire of naive mouse splenocytes. J Immunol, 2000. 164(11): p. 5782-7.
Chen, A.K., et al., Ratiometric bimolecular beacons for the sensitive detection of RNA in single living cells. Nucleic Acids Res, 2010. 38(14): p. e148.
Chen, Y.J., et al., DNA nanotechnology from the test tube to the cell. Nat Nanotechnol, 2015. 10(9): p. 748-60.
Corthay, A., K.S. Nandakumar, and R. Holmdahl, Evaluation of the percentage of peripheral T cells with two different T cell receptor alpha-chains and of their potential role in autoimmunity. J Autoimmun, 2001. 16(4): p. 423-9.
Dash, P., et al., Paired analysis of TCRalpha and TCRbeta chains at the single-cell level in mice. J Clin Invest, 2011. 121(1): p. 288-95.
Dekosky, B.J., et al., High-throughput sequencing of the paired human immunoglobulin heavy and light chain repertoire. Nat Biotechnol, 2013. 31(2): p. 166-9.
Dittmer, W.U., A. Reuter, and F.C. Simmel, A DNA-based machine that can cyclically bind and release thrombin. Angew Chem Int Ed Engl, 2004. 43(27): p. 3550-3.
Ewing, C., et al., Virus-specific CD8+ T-cell responses in mice transgenic for a T-cell receptor beta chain selected at random. J Virol, 1994. 68(5): p. 3065-70.
Taiwan Intellectual Property Office, Examination and Search Report for Taiwan app 106127772, dated Mar. 14, 2019.
Frame, K.K. and W.S. Hu, The loss of antibody productivity in continuous culture of hybridoma cells. Biotechnol Bioeng, 1990. 35(5): p. 469-76.

Franek, F. and J. Dolnikova, Hybridoma growth and monoclonal antibody production in iron-rich protein-free medium: effect of nutrient concentration. Cytotechnology, 1991. 7(1): p. 33-8.
Futschik, A. and C. Schlotterer, The next generation of molecular markers from massively parallel sequencing of pooled DNA samples. Genetics, 2010. 186(1): p. 207-18.
Han, D., et al., DNA gridiron nanostructures based on four-arm junctions. Science, 2013. 339(6126): p. 1412-5.
Han, D., et al., DNA origami with complex curvatures in three-dimensional space. Science, 2011. 332(6027): p. 342-6.
Hayakawa, K., et al., Isolation of high-affinity memory B cells: phycoerythrin as a probe for antigen-binding cells. Proc Natl Acad Sci U S A, 1987. 84(5): p. 1379-83.
Hurlbert, S.H., The Nonconcept of Species Diversity: A Critique and Alternative Parameters. Ecology, 1971. 52(4): p. 577.
International Search Report and Written Opinion for application PCT/US2017/046794, dated Oct. 30, 2017.
Johnson, P.L. and M. Slatkin, Inference of population genetic parameters in metagenomics: a clean look at messy data. Genome Res, 2006. 16(10): p. 1320-7.
Ke, Y., et al., Scaffolded DNA origami of a DNA tetrahedron molecular container. Nano Lett, 2009. 9(6): p. 2445-7.
Ke, Y., et al., Self-assembled water-soluble nucleic acid probe tiles for label-free RNA hybridization assays. Science, 2008. 319(5860): p. 180-3.
Kelso, G.F., et al., Impact on monoclonal antibody production in murine hybridoma cell cultures of adenosine receptor antagonists and phosphodiesterase inhibitors. Bioorg Med Chem Lett, 2016. 26(2): p. 540-4.
Ko, S., et al., DNA nanotubes as combinatorial vehicles for cellular delivery. Biomacromolecules, 2008. 9(11): p. 3039-43.
Li, X., Dynamic changes of driver genes' mutations across clinical stages in nine cancer types. Cancer Med, 2016.
Lynch, M., Estimation of nucleotide diversity, disequilibrium coefficients, and mutation rates from high-coverage genome-sequencing projects. Mol Biol Evol, 2008. 25(11): p. 2409-19.
Maniatis, T et al., "Molecular Cloning. A Laboratory Manual." Cold Spring Harbor, N.Y. pp. 280-281 (1982).
Mei, Q., et al., Stability of DNA origami nanoarrays in cell lysate. Nano Lett, 2011. 11(4): p. 1477-82.
Mhlanga, M.M., et al., tRNA-linked molecular beacons for imaging mRNAs in the cytoplasm of living cells. Nucleic Acids Res, 2005. 33(6): p. 1902-12.
Miconnet, I., Probing the T-cell receptor repertoire with deep sequencing. Curr Opin HIV AIDS, 2012. 7(1): p. 64-70.
Colwell, J. New Driver Mutations Detected in NSCLC. Cancer Discov, 2016.
Preston, F.W., The Commonness, and Rarity, of Species. Ecology, 1948. 29(3): p. 254-283.
Rani, L., et al., Immunoglobulin heavy chain variable region gene repertoire and B-cell receptor stereotypes in Indian patients with chronic lymphocytic leukemia. Leuk Lymphoma, 2016: p. 1-12.
Rinker, S., et al., Self-assembled DNA nanostructures for distance-dependent multivalent ligand-protein binding. Nat Nanotechnol, 2008. 3(7): p. 418-22.
Robins, H.S., et al., Comprehensive assessment of T-cell receptor beta-chain diversity in alphabeta T cells. Blood, 2009. 114(19): p. 4099-107.
Emerson R, et al, Estimating the ratio of CD4 + to CD8 + T cells using high-throughput sequence data, J Immunol Methods 391(1-2):14-21. 2013.
Fu J, et al., Interenzyme substrate diffusion for an enzyme cascade organized on spatially addressable DNA nanostructures, J Am Chem Soc 134(12):5516-9. 2012.
Kanda J, et al. Immune Recovery in Adult Patients Following Myeloablative Dual Umbilical Cord Blood, Matched Sibling, and Matched Unrelated Donor Hematopoietic Cell Transplantation, Biol Blood Marrow Transplant 18(11):1664-1676.e1. 2012.
Larimore K, et al, Shaping of Human Germline IgH Repertoires Revealed by Deep Sequencing, J Immunol 189(6):3221-30. 2012.
Robins HS, et al, Overlap and Effective Size of the Human CD8+ T Cell Receptor Repertoire, Sci Transl Med 2(47):47ra64. 2010.

(56) References Cited

OTHER PUBLICATIONS

Robins HS, et al, Ultra-Sensitive Detection of Rare T Cell Clones, J Immunol Methods 375(1-2):14-9. 2012.

* cited by examiner

HIGH THROUGHPUT OIL-EMULSION SYNTHESIS OF BOWTIE BARCODES FOR PAIRED MRNA CAPTURE AND SEQUENCING FROM INDIVIDUAL CELLS

CROSS-REFERENCE TO RELATED APPLICATIONS

This application represents the national stage entry of PCT International Application No. PCT/US2017/046794, filed on Aug. 14, 2017, and claims priority from and benefit of U.S. Provisional Application No. 62/377,123, filed on Aug. 19, 2016, the disclosures of which are incorporated by reference herein.

STATEMENT REGARDING FEDERALLY SPONSORED RESEARCH

This invention was made with government support under R21 CA196460 and R21 AI125827 awarded by the National Institutes of Health. The government has certain rights in the invention.

BACKGROUND

There are many biological questions that require single-cell analysis of multiple gene sequences, including analysis of clonally distributed dimeric immunoreceptors on lymphocytes and the accumulation of driver/accessory mutations in polyclonal tumors. Lysis of bulk cell populations results in the mixing of gene sequences, making it impossible to know which pairs of gene sequences originated from any particular cell and obfuscating analysis of rare sequences within large cell populations. Although current single-cell sorting technologies can be used to address some of these questions, such approaches are expensive, require specialized equipment, and lack the necessary high-throughput capacity for comprehensive analysis of large samples. Accordingly, there remains a need in the art for improved methods for genetic analysis of individual cells.

BRIEF SUMMARY

In a first aspect, provided herein is a method for incorporating single-stranded DNA (ssDNA) barcoded polynucleotides into a nucleic acid origami nanostructure. The method can comprise or consist essentially of (a) performing first strand synthesis of a barcode nucleic acid to generate double-stranded barcode nucleic acids, wherein the barcode nucleic acid comprises at least one priming site complementary to one side of a single-stranded 5'-5' bowtie linker nucleic acid comprising a central 5'-5' phosphodiester linker flanked on either side by complementary barcode nucleic acids and sequence(s) complementary to a nucleic acid origami nanostructure that may be conducted prior to or during subsequent oil-emulsion amplification steps; (b) combining the double-stranded barcode nucleic acids (or the single-stranded barcode and complementary primer pairs) and the 5'-5' bowtie linker nucleic acid in an oil-emulsion droplet comprising reagents for amplifying a target nucleic acid; (c) thermal cycling the oil-emulsion droplet comprising the double-stranded (or single-stranded) barcode nucleic acids primers and the 5'-5' bowtie linker nucleic acid sufficient to result in annealing of each strand from the double-stranded barcode nucleic acids to complementary sequences on the 5'-5' bowtie linker nucleic acid and elongation of ssDNA barcoded 5'-5' bowtie polynucleotides thereby yielding a product including barcoded mRNA capture sequences on either side of the 5'5' phosphodiester linkage bowtie strand; (d) extracting elongation products from the thermal cycled droplet; (e) purifying ssDNA barcoded 5'-5' bowtie polynucleotides from the extracted elongation products; and (f) incorporating the purified ssDNA barcoded 5'-5' bowtie polynucleotides into a nucleic acid origami nanostructure. Incorporating can comprise annealing the purified ssDNA barcoded 5'-5' bowtie polynucleotides to a nucleic acid origami nanostructure. The nucleic acid origami nanostructure can be a DNA nanostructure.

In another aspect, provided herein is a method for detecting target nucleic acid sequences at the single cell level. The method can comprise or consist essentially of (a) contacting a nucleic acid origami nanostructure obtained according to the method of claim 1 to nucleic acids isolated from a single cell, wherein the nanostructure comprises ssDNA barcoded polynucleotides having barcoded sequences complementary to target nucleic acid sequences; and wherein contacting occurs under conditions suitable for binding of the barcoded sequences to the target nucleic acid sequence if present in the single cell; (b) recovering target nucleic acid sequences bound to the barcoded sequences; and (c) reverse transcribing the recovered target nucleic acid sequences using the ssDNA barcoded polynucleotides as gene-specific primers for reverse transcription, whereby target nucleic acids, if present in the cell, are detected without a single-cell sorting step. The nucleic acid origami nanostructure can be a DNA nanostructure.

In a further aspect, provided herein is a method for detecting B cell receptor sequences at the single cell level. The method can comprise or consist essentially of (a) transfecting into an antigen-specific B cell expressing unique heavy (IgH) and light (IgL) chain BCR mRNA; (b) contact a DNA origami nanostructure comprising multiple barcoded mRNA capture sequences to capture and protect both immunoglobulin heavy (IgH) and light (IgL) chain BCR mRNA in transfected antigen-specific B cells; (c) isolating the contacted DNA origami nanostructures to recover IgH and IgL mRNA bound to the barcoded mRNA capture sequences; and (d) reverse transcribing the recovered IgH and IgL mRNA using the barcoded mRNA capture probes as gene-specific primers for reverse transcription, whereby target BCR sequences are detected without a single-cell sorting step. The DNA origami nanostructures can comprise integral biotin labels and wherein isolating the contacted nanostructures comprises avidin column purification.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The present invention will be better understood and features, aspects, and advantages other than those set forth above will become apparent when consideration is given to the following detailed description thereof. Such detailed description makes reference to the following drawings, wherein:

FIGS. 2A-2C illustrate DNA origami design and synthesis. (A) Organization of 5'-5' bowtie mRNA capture probe. Various regions allow for incorporation into DNA origami nanostructures, downstream PCR amplification, barcode pairing, and IgH/IgL mRNA capture. (B) Schematic visualization of 5'-5' bowtie mRNA capture probe extending from the surface of an origami nanostructure while annealing with BCR IgH and IgL mRNA (note: the length of the 5'-5' bowtie capture probes has been exaggerated to allow for visualization of the structure). (C) Validation of properly folded DNA origami molecules as visualized by AFM showing the anticipated "wafer" shape (probes are too flexible to be visualized by AFM). Each origami molecule is roughly 60×90 nM in scale.

FIGS. 5A-5B demonstrate transfection of primary lymphocytes with DNA origami nanostructures. (A) Lymphocytes from mice were mock transfected (left) or transfected with FITC-labeled DNA origami nanostructures (middle). Transfected cells were visualized based on detection of FITC label by flow cytometry. To ensure that origami structures were being taken up by cells and not bound to the cell surface, cells were treated with DNase after transfection. A similar FITC signal was detected from the DNA origami following DNase treatment (right). (B) DNase digestion destroys DNA origami on the cell surface after incubation, as confirmed by gel electrophoresis.

FIG. 6 is a flowchart illustrating an exemplary Next Generation Sequencing (NGS) analysis protocol. Sequences from individual runs are parsed into FASTQ files for alignment using BWA-MEM software. Analysis files are generated for mapping, read count, and junction detection, and further processed for quality control of sequences and amplification bias.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

Figure 1:
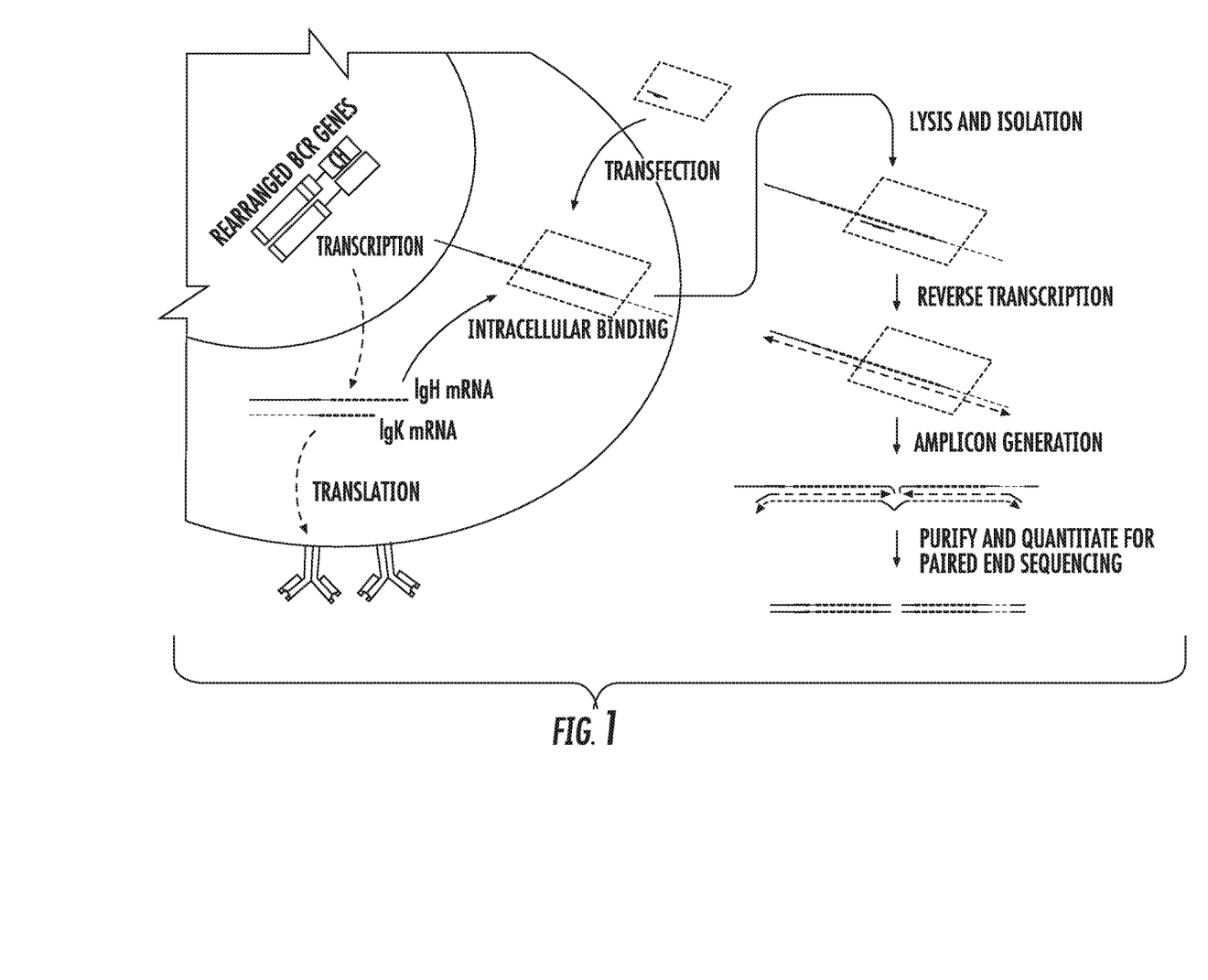
FIG. 1 is a schematic of an exemplary method of using DNA origami nanostructures to obtain linked sequence information from BCR/antibody mRNAs from single cells without single-cell sorting. Antigen-reactive B cells are obtained by flow cytometry cell sorting using fluorescently labeled antigens and transfected by electroporation with DNA origami nanostructures containing extended sequences complementary to both IgH and IgL (i.e., κ or λ) constant region mRNA. DNA origami molecules bind and protect intracellular IgH and IgL mRNA within individual cells that are then lysed, and origami with bound mRNA are then reisolated and purified. Using the mRNA capture probes as reverse transcription primers, IgH and IgL gene sequences are extended on the origami capture probes. The cDNA is then further amplified by standard IgH/IgL V-gene multiplex PCR to obtain a pool of amplification products suitable for Illumina paired-end sequencing. Each amplicon contains a 12-mer barcode that can be paired to its complement, thus providing sequence information for both IgH and IgL mRNA from an individual cell without the need for single-cell sorting.

The inventors previously developed novel DNA origami nanostructures having the capacity to capture and protect mRNA sequences from transfected cells. Integral fluorescent labels on the DNA origami facilitate identification of transfected cells, and reisolation of the nanostructures with bound mRNA is achieved using integral biotin labels and avidin column purification. The methods provided herein are based at least in part on the inventors' discovery of a robust methodology for pairing multiple genes of interest from individual cells without the need for single cell sorting or specialized equipment (FIG. 1). The present disclosure provides novel methods for incorporating "bowtie-barcode" technology into DNA origami nanostructures and other nucleic acid-based nanostructures to allow for simultaneous pairing and capture of mRNAs from millions of cells. Additional improvements in microporation (using microliter volumes for cell electroporation) technology have increased transfection efficiency and improved cell viability. Finally, the combination of the bowtie-barcode capture methods with oil-water emulsion droplet based systems and overlap extension PCR enables the creation of millions of paired, random sequences that can be utilized as barcodes to link individual genetic sequences back to one another during sequencing. By linking mRNAs through unique matching barcoded sequence analysis, the inventors developed a cost-effective method useful for analyzing large cell populations and easily adaptable for probing sequence diversity of paired genes from virtually any heterogeneous cell population.

With respect to other transfectable nucleic acid hybridization platforms, no other successful molecular approaches exist for an analysis requiring the linking of multiple mRNA species. While transfection of single stranded oligos has been attempted, the single stranded oligos activate the RISC complex and are degraded, precluding downstream analysis. Without being bound to any particular mechanism or theory, it is believed that the semi-supercoiled nature of the origami molecules inhibits degradation by the RISC complex, as evidenced by the ability to re-capture and isolate transfected origami molecules with bound mRNAs. Additionally, in reference to standard single-celled emulsion-based systems, they were not suitable for analysis requiring the linking of multiple mRNA species. While the emulsion-based system allows for input of higher cell numbers than single cell sorting, prior art single-celled emulsion-based systems only captured 7 paired sequences (>0.000001%) and were unable to detect the presence of their control at a concentration less than 1000/1000000. While most clones are believed to exist as a single clone per person, this level of sensitivity would not be acceptable for discovery of rare cells.

Accordingly, in a first aspect, provided herein is a method of incorporating single-stranded DNA (ssDNA) barcoded polynucleotides into a nucleic acid origami nanostructure. The method comprises, or consists essentially of, the following steps: (a) performing first strand synthesis of a barcode nucleic acid (either prior to or during subsequent oil-emulsion steps) to generate complementary double-stranded barcode nucleic acids, where the barcode nucleic acid comprises at least one priming site complementary to one portion of a single-stranded bowtie linker DNA strand comprising a central 5'-5' phosphodiester linker flanked by sequences complementary to the barcode nucleic acids and sequence(s) complementary to a nucleic acid origami nanostructure; (b) combining the double-stranded barcode nucleic acids (or single-stranded barcode nucleic acids and complementary priming sets) and the 5'-5' bowtie linker nucleic acid in an oil-emulsion droplet comprising reagents for elongating a target nucleic acid; (c) thermal cycling the oil-emulsion droplet comprising the double-stranded barcode nucleic acids (or single-stranded barcode nucleic acids and complementary primers) and the 5'-5' bowtie linker nucleic acid sufficient to result in annealing of each strand from the double-stranded barcode nucleic acids to complementary sequences on the 5'-5' bowtie linker nucleic acid and elongation of single stranded DNA (ssDNA) barcoded 5'-5' bowtie polynucleotides thereby yielding an elongation product droplet; (d) extracting elongation products from the droplet; (e) purifying ssDNA barcoded 5'-5' bowtie polynucleotides from the extracted elongation products; and (f) incorporating the purified ssDNA barcoded 5'-5' bowtie polynucleotides into a nucleic acid origami nanostructure.

As used herein, the term "barcode" refers to unique sequences of nucleotides that can be used to distinguish, pair, and uniquely identify nucleic acids from the same cell. In some cases, barcodes may be used to distinguish tens, hundreds, or even thousands of nucleic acids, e.g., arising from different cells or other sources. As used herein, the term "bowtie-barcode" refers to a set of complementary barcode sequences linked together via a unique 5'-5' non-standard phosphodiester DNA "bowtie" structure, meaning a central phosphodiester linker flanked on either side by complementary barcode nucleic acid sequences.

As used herein, the term "nucleic acid nanostructure" is used for convenience and it is to be understood that the invention contemplates nucleic acid nanostructures generally. The nanostructures of the invention may be linear (e.g., nanorods) or non-linear (e.g., star-shaped, triangular, etc.). Nucleic acids such as DNA or RNA may be folded into predetermined one-, two- or three-dimensional nanostructures using a variety of techniques, such as DNA or RNA origami.

The terms "oligonucleotide," "nucleotide," and "nucleic acid" are used interchangeably to mean molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). Thus, the term embraces both DNA and RNA oligonucleotides. The terms shall also include polynucleosides (i.e., a polynucleotide minus the phosphate) and any other organic base-containing polymer. Oligonucleotides can be obtained from existing nucleic acid sources (e.g., genomic or cDNA), but are preferably synthetic (e.g., produced by nucleic acid synthesis).

Figure 2A:
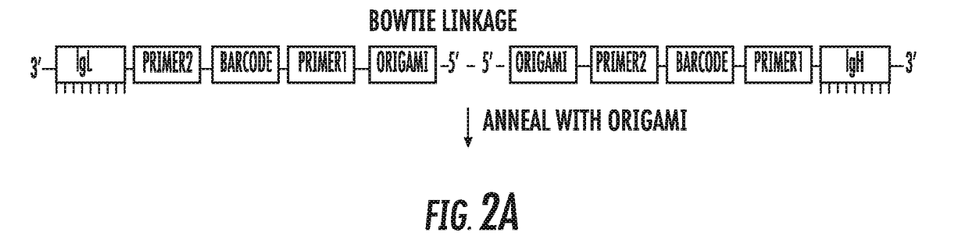

Construction of barcoded 5'-5' bowtie linker capture probes: Barcoded polynucleotides are long ssDNA strands, constructed containing a central 5'-5' "bowtie" linkage, allowing for both ends to run 5'→3'. The bowtie linkages can comprise a pre-synthesized DNA sequence (e.g., ordered from commercial vendor). Preferably, either end of a barcoded polynucleotide additionally may comprise a specific sequence complementary to the M13mp18 phage DNA origami backbone. This sequence can be varied and adapted for barcode incorporation into any target nanostructure. Referring to FIG. 2A, either end can additionally comprise a conserved PCR primer site for downstream amplification, a unique barcode complementary to the barcode on the opposing end of the strand, a second conserved priming site, and an mRNA capture site complementary to a conserved region of the genes of interest. An important design feature of the capture sequences is that mRNAs are paired to one another by a unique set of complementary nucleotide barcodes contained on either end of the 5'-5' bowtie strand.

Figure 2B:
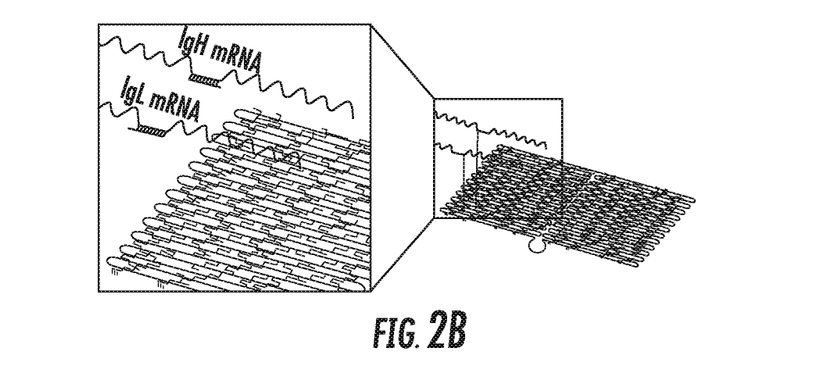
Figure 2C:
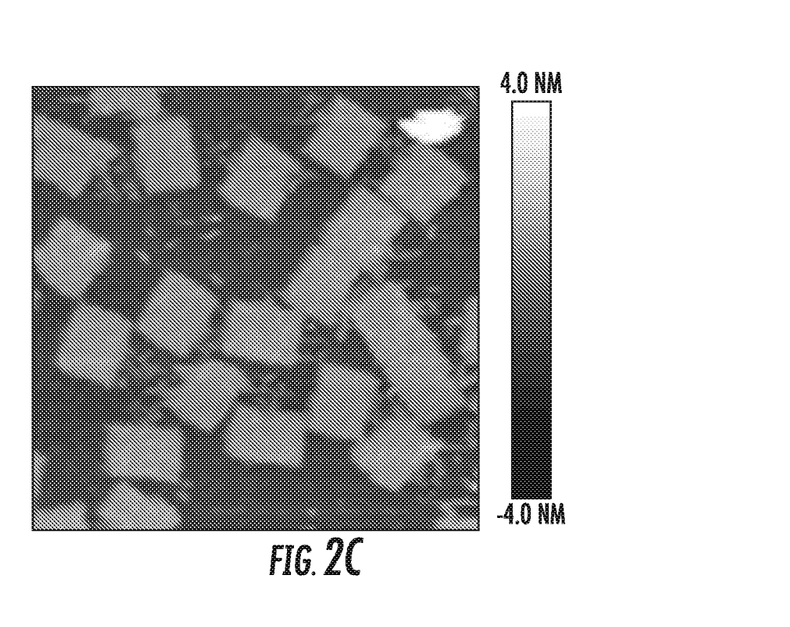

The long barcoded bowtie polynucleotide can then be incorporated into the DNA origami mastermix (or other desired nanostructure) and the M13mp18 complementary sequence(s) in the barcode bowtie self-assemble with the origami nanostructure. Referring to FIG. 2B, the mRNA capture sequence regions of the bowtie extend from the surface of the origami nanostructure. In some cases, incorporating a ssDNA 5'-5' barcoded bowtie polynucleotide into a nucleic acid nanostructure can comprise annealing.

As described herein, oil-emulsion droplets can be used to incorporate a unique set of complementary barcodes into millions (or more) bowtie strands. Base bowtie strands comprising central 5'-5' non-traditional phosphodiester linkages can include sequence(s) complementary to sequences of a nucleic acid origami nanostructure as well as two different conserved priming sites, which are procured from a commercial vendor (e.g., Integrated DNA Technologies, Inc.). In some cases, the 5'-5' bowtie strand has, for example, the following sequence:

```
                                           (SEQ ID NO: 1)
3'-CGAGTCCCTTTATCGGGAAC-5'-5'-GAACGTGGCGAGAAAG
GAAGGGAACAAACTATGGACAGCAAAGACAGCACCT-3'.
```

In some cases, the barcode strand has the following sequence:

(SEQ ID NO: 2)
5'CACCGACTTTGACTCCCAAATCAATGTGCGGACAGCAAAGACAG
CACCTNNNNNNNNNNNNNGCTCAGGGAAATAGCCCTTGGGGTAGCCT
TTTGTTTGTTTGCAATCTCTG3', where "N" can be any of the four nitrogen bases found in DNA (adenine, cytosine, guanine, or thymine).

Figure 3A:
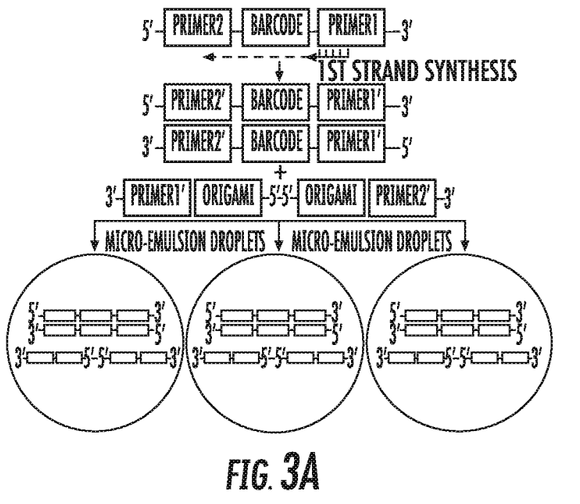
FIGS. 3A-3C illustrate construction of 5'-5' bowtie mRNA capture probes containing complementary barcode sequences. (A) Following first strands synthesis of 10-mer barcode strands, a 1:1:1 barcode: 5'-5' strand:oil-water emulsion droplet reaction is set up. (B) Overlap extension of the 5'-5' strands using the barcode strands as templates allows for complementary barcodes to be incorporated on either end of the 5'-5' strands. (C) Following denaturing PAGE purification, adapter strands are utilized to perform a modular T4 DNA ligation reaction, to attach gene-specific complementary mRNA capture sequences to either end of the 5'-5' strand. After a final denaturing PAGE purification and quantification, the barcoded 5'-5' mRNA capture probes can be incorporated into individual DNA origami nanostructures.

In other cases, the barcode labeled strands comprise one priming site that is complementary to one side of a 5'-5' bowtie strand; a random 10-mer nucleotide barcode ($4^{10}=1048576$ unique barcodes, if $>10^6$ sequences are analyzed an 11-mer or 12-mer barcode may be employed); and a second priming site that is complementary to the other side of the 5'-5' bowtie strand with specific mRNA (complementary) capture sequences flanking both ends of the barcode strand. Short barcode strands may be used in a first-strand-synthesis reaction to create dsDNA products with complementary barcodes or used downstream in standard polymerase chain reaction (PCR) reactions during the oil-emulsion elongation step to synthesize the dsDNA barcode strands directly in the emulsion droplet. Referring to FIG. 3A, $>10^{10}$ identical ssDNA 5'-5' bowtie strands and unique dsDNA barcode strands (or ssDNA barcode strands with complementary primers) are then incorporated at a 1:1:1 molecule-to-molecule-to-droplet ratio in an oil-water emulsion droplet overlap extension elongation system. Standard PCR cycles can be used to denature the dsDNA barcode strands (or amplify the ssDNA barcode strands followed by denaturation), to anneal both ssDNA strands from the dsDNA barcode strands with either end of a 5'-5' bowtie, and to elongate the bowtie using the ssDNA barcode strands as a template.

Figure 3B:
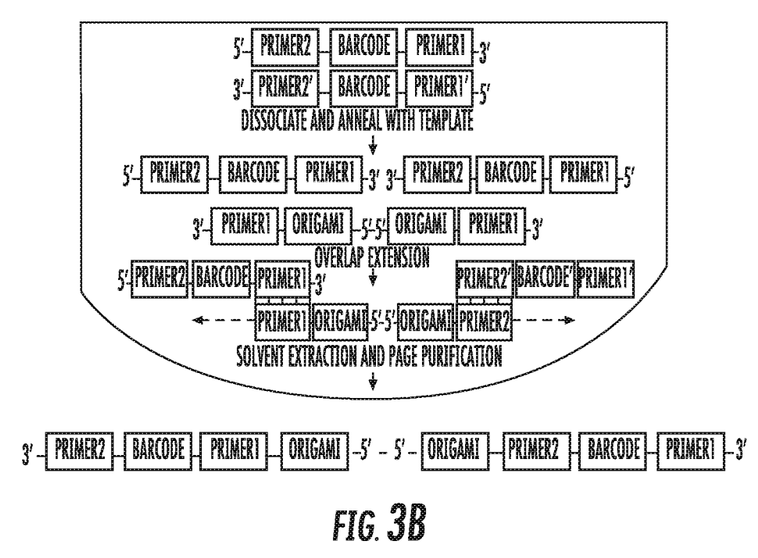
Figure 3C:
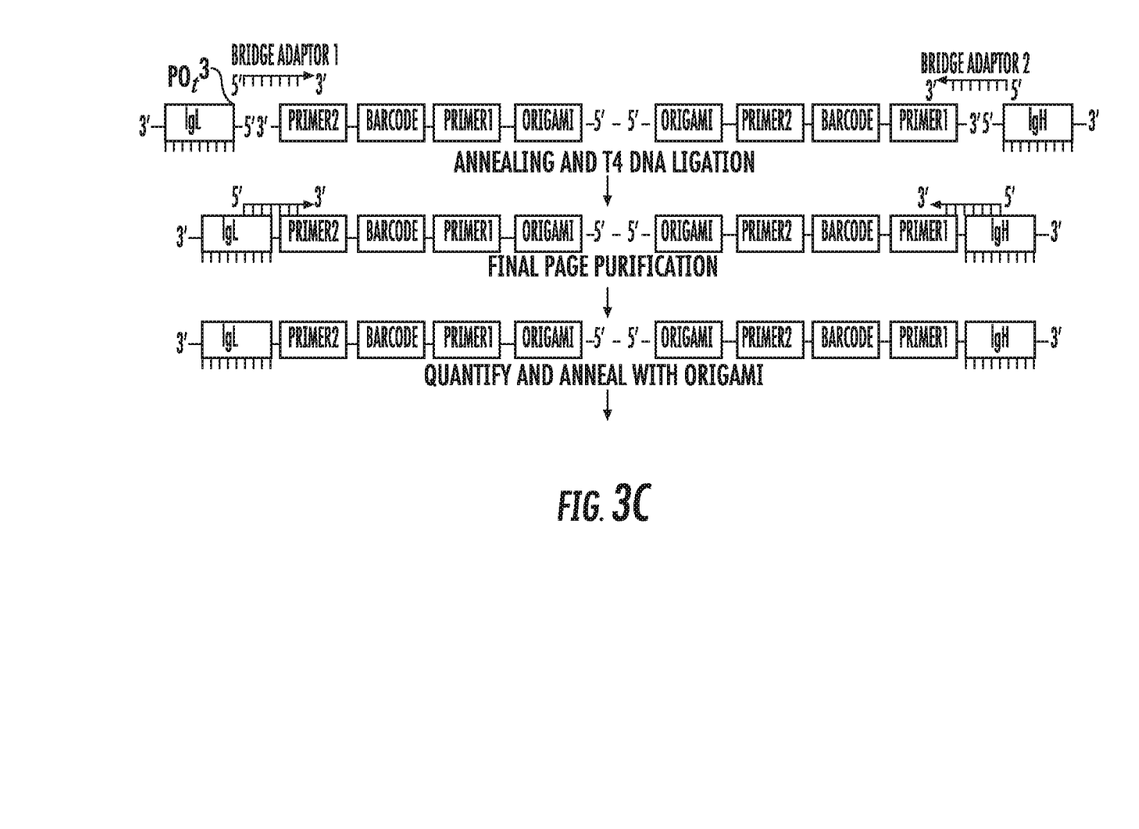

After denaturation, overlap extension is carried out in each droplet as each of the strands from the dsDNA barcode will anneal with its complementary priming site on the 5'-5' bowtie linker, acting as a primer and template for overlap extension, and thus incorporating complementary 10-mer barcodes on either end of the 5'-5' bowtie strands as well as mRNA specific capture sequences on the 3' ends of the bowtie strands (FIG. 3B). While this system is not an exponential PCR amplification, multiple dissociation/annealing/elongation cycles are employed to ensure both ends of each 5'-5' linker are elongated. PCR products are then extracted from the oil-water emulsion system using a standard ether/ethyl acetate extraction protocol, and ssDNA barcoded 5'-5' bowtie strands are purified from remaining nucleic acids by standard denaturing PAGE purification. Products at this point will contain (in order from 5'-5' central bowtie linkage extending towards both 3' ends) the following: origami complementary sequence (may be one side only), a conserved PCR priming site, a random 10-mer barcode complementary to the barcode on the opposing arm of the 5'-5' linkage, and a second conserved priming site, and gene specific mRNA capture sequences (FIG. 3B). Following the final denaturing PAGE purification, final products will contain regions necessary for: 1) incorporation into the DNA origami structure, 2) conserved priming sites for downstream PCR amplification, 3) complementary barcodes utilized for pairing both captured mRNAs, and 4) mRNA capture sequences complementary to conserved regions of genes of interest that can also be used as gene-specific reverse transcription primers (FIG. 3C).

These unique bowtie barcodes can then be incorporated into individual origami molecules or any nucleic acid structure of interest by simply changing the identity of the "origami annealing sequence" portion of the strand. This method allows for extreme levels of mRNA pairing specificity due to the uniquely barcoded mRNA capture sequences attached to each bowtie strand.

The recovered mRNAs are reverse transcribed (RT) into cDNA using conserved sequences on the capture strands as gene-specific RT primers, thereby extending the gene-specific cDNA from the 3' ends of the bowtie-barcodes. Since the conserved gene-specific sequences on the bowtie barcodes are required for priming the RT reaction, any unbound mRNAs will not be amplified, thus improving selectivity and avoiding false pairing.

Reverse transcription and barcode-linked mRNA amplicon generation (FIG. 1): Once mRNA-bound origami has been purified from cell lysate, reverse transcription (RT) will be performed. Using the mRNA complementary regions of the bowtie barcodes as RT primers, elongation can be achieved by simply adding any commercially available RT mastertnix, and incubating per manufacturer's recommendations. The mRNA can then be removed by addition of a commercial RNaseH cocktail, and barcoded cDNA will be obtained as extended products from the 3' ends of the barcode bowties. We have previously validated this approach using in vitro transcribedtarget mRNA-bound origami and confirmed the ability to isolate gene specific cDNA by PCR. Finally, a multiplex PCR using a single primer for both of the conserved priming sequences on either end of the bowtie barcodes, and, depending on the application of the technology, 1) the well-established multiplex primer sets for the TCRα/TCRβ V-genes or IgH/IgL V-families can be performed to generate a pool of amplicons with corresponding CDR3 regions of immunoreceptors or 2) a single primer for a conserved region just outside of the mutation of interest in known cancer driver/co-driver genes, will result in barcode-paired PCR products. By inclusion of Illumina-specific adapter sequences in the primer sets, barcoded amplicons with CDR3 sequences, cancer mutation sequences, or any paired gene sequences of interest from heterologous cell populations can be obtained that are immediately suitable for use in standard Illumina paired-end sequencing.

In another aspect, provided herein are methods for the parallel capture, barcoding, and quantification of a panel of tens to hundreds, or more, of specific DNA and/or RNA sequences from large numbers of single cells, e.g., for the purpose of profiling cell populations or other purposes. In preferred embodiments, a method for detecting target nucleic acid sequences at the single cell level comprises, or consists essentially of, the following steps: (a) contacting a nucleic acid origami nanostructure obtained according to the method of claim 1 to nucleic acids isolated from a single cell, wherein the nanostructure comprises ssDNA barcoded polynucleotides having barcode sequences complementary to target nucleic acid sequences; and wherein contacting occurs under conditions suitable for binding of the barcode sequences to the target nucleic acid sequence if present in the single cell; (b) recovering target nucleic acid sequences bound to the barcode sequences; and (c) reverse transcribing the recovered target nucleic acid sequences using the ssDNA barcoded polynucleotides as gene-specific primers for reverse transcription, whereby target nucleic acids, if present in the cell, are detected without a single-cell sorting step.

In a further aspect, provided herein is a method for detecting B cell receptor sequences at the single cell level. The method comprises, or consists essentially of, the following steps: (a) transfecting into an antigen-specific B cell;

(b) contact a DNA origami nanostructure comprising one or more sets of mRNA capture sequences to capture and protect both immunoglobulin heavy (IgH) and light (IgL) chain BCR mRNA in transfected antigen-specific B cells (c) isolating the contacted DNA origami nanostructures to recover IgH and IgL mRNA bound to the one or more mRNA capture sequences; and (d) reverse transcribing the recovered IgH and IgL mRNA using the one or more sets of mRNA capture probes as gene-specific primers for reverse transcription, whereby target BCR sequences are detected without a single-cell sorting step.

In some cases, the DNA origami nanostructures comprise integral biotin labels, and the step of isolating the contacted nanostructures can comprise avidin column purification.

A nucleic acid or nucleic acid molecule, as used herein, can include any nucleic acid of interest. In some embodiments, nucleic acids include, but are not limited to, DNA, RNA, peptide nucleic acid, morpholino nucleic acid, locked nucleic acid, glycol nucleic acid, threose nucleic acid, mixtures thereof, and hybrids thereof, or nucleic acids with internal carbon backbone spacers. In some aspects, a nucleic acid is a "primer" capable of acting as a point of initiation of synthesis along a complementary strand of nucleic acid when conditions are suitable for synthesis of a primer extension product. Nucleic acids may be single-stranded, double-stranded, and also tripled-stranded. In some aspects, the nucleic acid serves as a template for synthesis of a complementary nucleic acid, e.g., by base-complementary incorporation of nucleotide units. For example, in some aspects, a nucleic acid comprises naturally occurring DNA (including genomic DNA), RNA (including mRNA), and/or comprises a synthetic molecule including, but not limited to, complementary DNA (cDNA) and recombinant molecules generated in any manner. In some aspects, the nucleic acid is generated from chemical synthesis, reverse transcription, DNA replication or a combination of these generating methods.

Nucleic acids can be obtained using any suitable method, including those described by Maniatis et al., Molecular Cloning: A Laboratory Manual, Cold Spring Harbor, N.Y., pp. 280-281 (1982). In some aspects, nucleic acids are obtained as described in U.S. Patent Application Publication No. US2002/0190663. Nucleic acids obtained from biological samples typically are fragmented to produce suitable fragments for analysis.

Nucleic acids and/or other moieties of the invention may be isolated. As used herein, "isolated" means separate from at least some of the components with which it is usually associated whether it is derived from a naturally occurring source or made synthetically, in whole or in part. Nucleic acids and/or other moieties of the invention may be purified. As used herein, "purified" means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one,".

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Examples.

EXAMPLES

Example 1—Reverse Transcription and Barcode-Linked mRNA Amplicon Generation

Once mRNA-bound origami has been purified from cell lysate, reverse transcription (RT) is performed. Using the mRNA complementary regions of the bowtie barcodes as RT primers, elongation is achieved by adding any commercially available RT mastermix, and incubating per the manufacturer's recommendations. The mRNA is removed by addition of a commercial RNaseH cocktail, and barcoded cDNA is obtained as extended products from the 3' ends of the barcode bowties. We previously validated this approach using in vitro transcribedtarget mRNA-bound origami and confirmed the ability to isolate gene specific cDNA by PCR. Finally, multiplex PCR is performed using a single primer for each of the conserved priming sequences on either end of the bowtie barcodes. Depending on the application of the technology, (1) the well-established multiplex primer sets for the TCRα/TCRβ genes or BCR IgH/IgL V-families are to generate a pool of amplicons with corresponding CDR3 regions of immunoreceptors; or (2) a single primer for a conserved region just outside of the mutation of interest in known cancer driver/co-driver genes is used to obtain barcode-paired PCR products; or (3) a single primer for a conserved region adjacent to heterologous genes within diverse organismal species or cell populations. By inclusion of Illumina-specific adapter sequences in the primer sets, barcoded amplicons with CDR3 sequences are obtained that are immediately suitable for use in standard Illumina paired-end sequencing.

Example 2—DNA Origami Binding to Immunoreceptor mRNA

Figure 4:
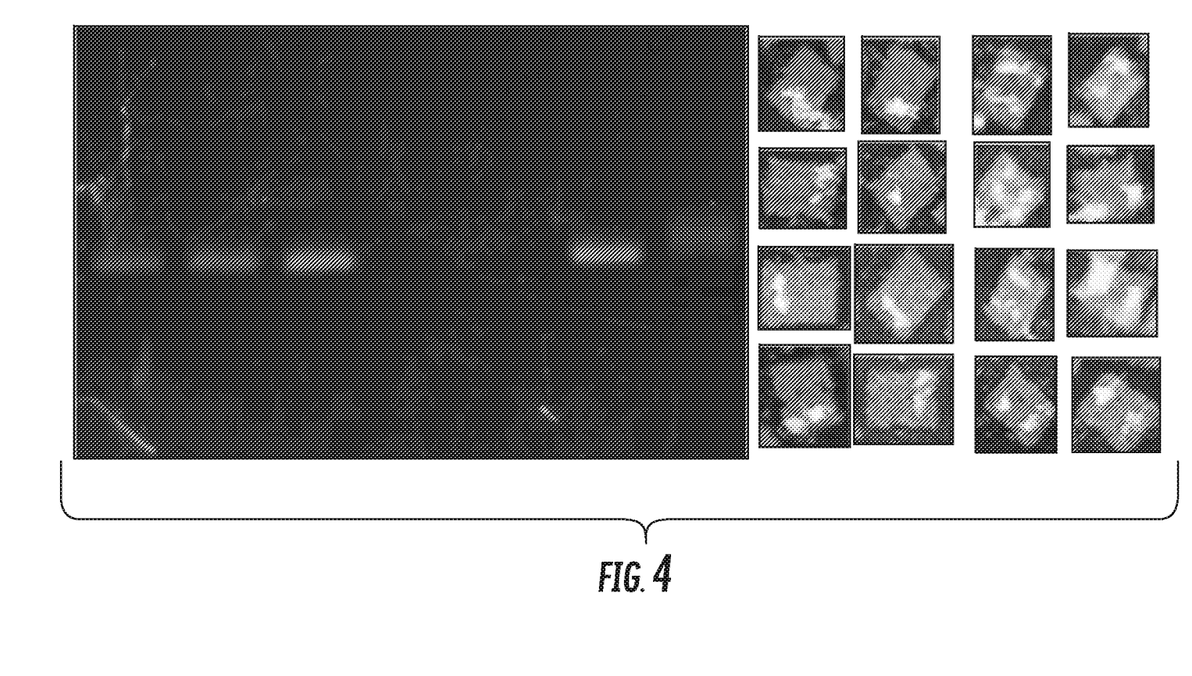
FIGS. 4A-4C demonstrate binding of DNA origami nanostructures to target mRNA. (A) Target mRNA binds specifically to the DNA origami structures: Shift of DNA origami due to specific binding of target mRNA was visualized using a reporter fluorescein molecule. Lanes 1-3: DNA origami without target-specific extended staple sequences incubated with in vitro transcribed target mRNA (1), alone (2), or with nonsense (scrambled) mRNA (3). Lane 4: In vitro transcribed target mRNA only (not visible), Lane 5: MW marker (not visible), Lanes 6-7: DNA origami with extended target-specific staple sequences incubated alone (6) or with in vitro transcribed target mRNA (7). The specific FRET signal identifies DNA origami structures. (B) Selected AFM images show specificity of in vitro transcribed target mRNA bound to origami with target-specific extended staples but not to non-target staples (mRNA visible only on one side of the origami molecule). (C) Selected AFM images show binding of two in vitro transcribed target mRNAs, captured by individual origami containing both alpha and beta staples (mRNA bound on both sides of origami molecules).

We previously developed the following approach for analysis of heterodimeric T cell receptors (TCR), which pose similar problems in terms of diversity and heterogeneous cell populations. FIGS. 4A-4C present preliminary data in the context of analysis of a known transgenic TCR (P14 transgenic T cells). Origami nanostructures were designed to comprise multiple mRNA capture probes per individual origami molecule. We have since modified our nanostructure design to incorporate a single 5'-5' barcoded mRNA capture strand per origami molecule. While the mRNA binding kinetics are assumed to be similar, optimization experiments will be performed to evaluate mRNA binding efficiency. Previously, when origami containing both TCRα- and TCRβ-specific probes were incubated with TCRβ mRNA only, mRNA was only captured by one side of the origami molecule (presumably with TCRβ-specific probes) (FIG. 4B). When origami containing both TCRα- and TCRβ-specific probes was incubated with both TCRα and TCRβ mRNA, both sides of the origami captured mRNA indicating both types of TCR mRNA were bound to corresponding probes on either side of individual origami molecules (FIG. 4C), confirming the capability and specificity of correct mRNA binding. Again, for our prior experiments analyzing TCR mRNA binding, we utilized individual probe strands on either side of the origami molecule, complementary for either TCRα or TCRβ sequences respectively. Although capture of mRNA will occur in a slightly different orientation, no significant change in origami-mRNA capture is expected.

Example 3—Transfection of DNA Origami Nanostructures

Previous studies have utilized receptor-mediated endocytosis of DNA nanostructures via the caveolin-dependent pathway leading to microtubule transport to lysosomes and therefore breakdown of the nanostructure. The obvious problem with this strategy is that for mRNA capture and subsequent reisolation, our nanostructures must bypass the endocytosis pathway, and instead cross the membrane directly to the cytoplasm. Electroporation is the simplest method for cytoplasmic entry and thus avoidance of the deleterious effects of endosomal degradation. However high cell mortality rates have commonly been associated with this methodology. Recent advancements in microporation technology (the use of µL volume electroporations) have shown high transfection efficiencies (>93%) as well as high cell viabilities (>86%). For our B cell transfection experiments we will use KL25 IgL/IgH transgenic mice expressing the same KL25 sequence BCR as the hybridoma that were previously generated [34]. Splenocytes from 4-to 6-week-old KL25 IgL/IgH transgenic mice will be prepared by mechanical disruption and red blood cell lysis in 0.83% $NH_4Cl$. IgM+B cells will be purified by magnetic cell sorting and >95% purity of sorted populations will be confirmed by flow cytometry. Cells will be pelleted by centrifugation (1200 rpm, 5 minutes, 4° C.), washed with OPTI-MEM™ media (Gibco), and resuspended in OPTI-MEM™ media at $1 \times 10^7$ cells/mL. For electroporation, a Neon syringe transfection system (Thermo Scientific) will be used with 100 µL syringe tips at the following settings: 2000 V, 10 ms, 1 pulse. Samples will consist of 100 µL cell suspensions and either 25 µL (20 nM) DNA origami suspension (in 1X TAE-$Mg^{2+}$) or a mock transfection control of 25 µL 1X TAE-$Mg^{2+}$ buffer. Immediately following electroporation, cells will be transferred to fresh RPMI-1640 culture medium with 10% fetal calf serum and incubated at 37° C. for 12-24 hours in individual wells of a 96 well plate. To assess transfection efficiency, cells will be visualized on a LSR Fortessa flow cytometer; the fluorescein isothiocyanate (FITC; 488 nm excitation, 518 nm emission) tag incorporated into each nanostructure allows for successfully transfected cells to be identified by flow cytometry.

Figures 5A, 5B:
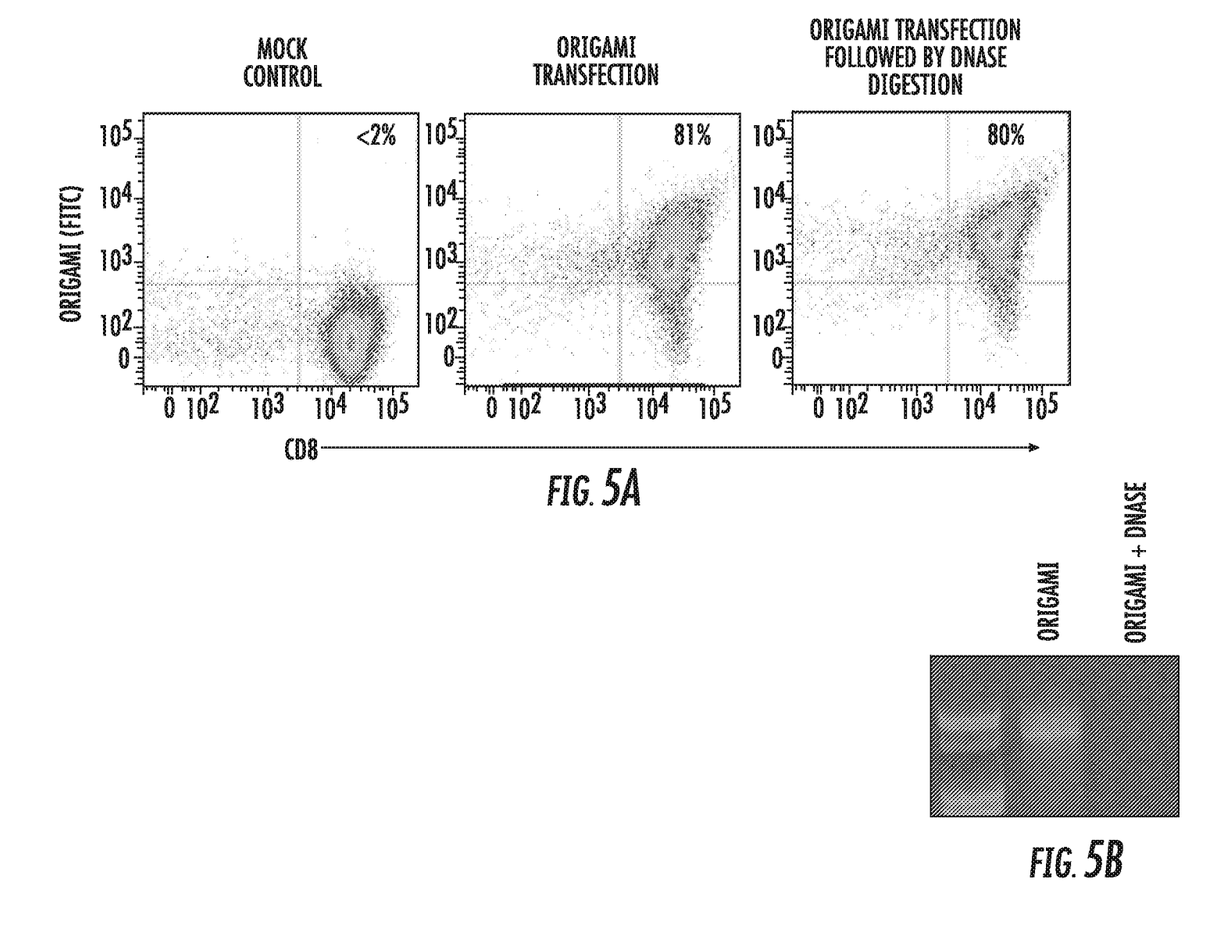

We previously developed this transfection protocol for mouse primary T lymphocytes (FIG. 5A) and anticipate that similar settings will provide initial starting points for B cell transfection. In our previous experiments, we verified that the DNA origami nanostructures enter transfected lymphocytes rather than binding non-specifically to the cell surface that would give false-positive readings by treating transfected cells with concentrated DNase (Turbo DNase, Ambion, Life Technologies) and then analyzed the cells for successful transfection by FACS analysis (FIG. 5A). We also confirmed that concentrated DNase treatment resulted in the successful destruction of DNA nanostructures (FIG. 5B). Thus, DNA origami has excellent transfection efficiency for primary lymphocytes. It should be noted that Turbo DNase is a proprietarily engineered version of DNaseI and has a markedly higher affinity for DNA than wild type DNaseI, which we found to be much less effective at degradation of origami nanostructures. Additionally, our group has previously demonstrated that DNA origami are highly stable in cell Lysate for 12 hours [33], confirming these structures are resistant to cytosolic nuclease degradation.

Example 4—Sequence Data Management, Processing and Analysis (Prophetic)

Figure 6:
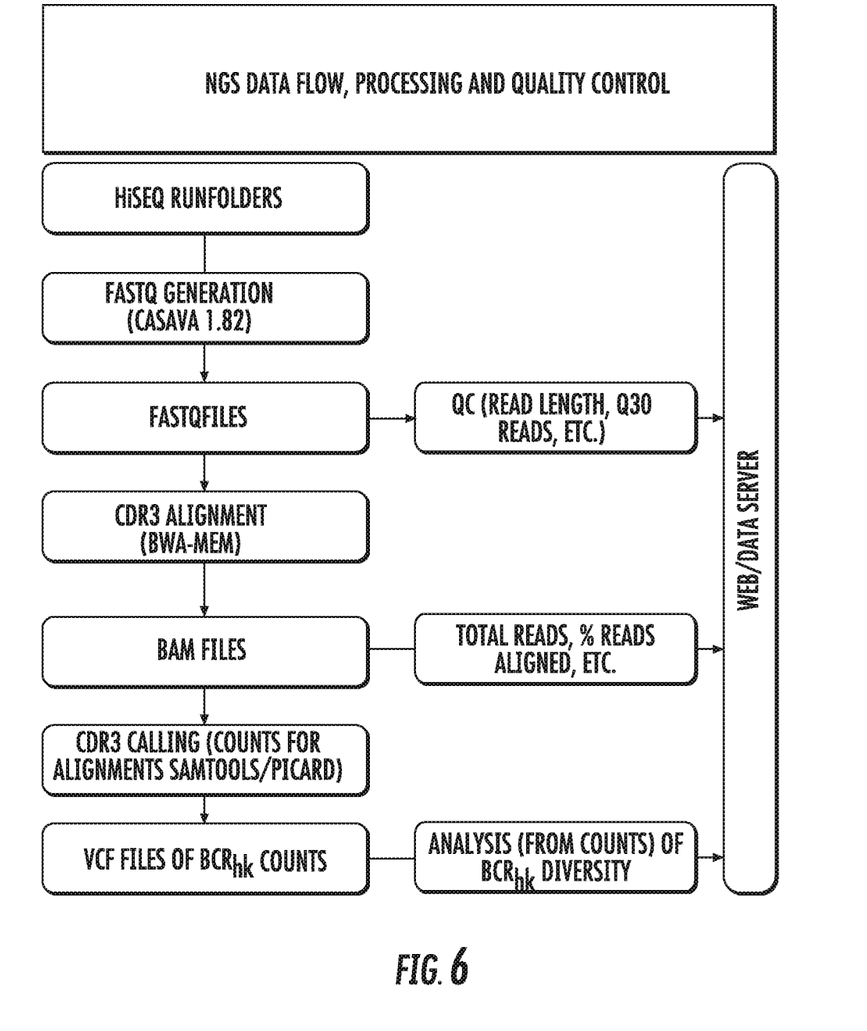

The success of this project depends on a validated data processing pipeline and an experienced informatics team responsible for managing, processing, and sharing massive amounts of data. Accordingly, a validated pipeline for analyzing paired whole-genome and transcriptome next-generation sequencing data, such as a Next-Generation Data Processing and Analysis Pipeline, which utilizes validated software tools and produces standard platform-independent formats (FIG. 6), is used. At each step within the pipeline, statistics files are created to ensure that all processes have been completed and the files are uncorrupted. Statistics files contain "aligned bases," "mismatch rate," and "md5sums." Early within a pipeline, several additional checks are invoked, including estimates of overall library coverage, library consistency, quality of bases, and contamination checks. This pipeline is built around (1) standardized file formats, (2) multiple quality control checks, (3) automated processing, (4) scheduled releases of sequence data, sequencing alignments, and variant calls, and (5) centralized primary data processing.

Reads are subjected to a series of quality control steps for quantifying biases at any given base, and then are parsed into independent FASTQ files for alignment using BWA-MEM for accurate split-read alignment of the unique CDR3 structures. Each sequence has a 12 nucleotide match to one of the $V_\kappa$ or $V_H$ gene segments, corresponding to the CASS consensus amino acid sequence from the second conserved cysteine at the 3' end of the V segment, as well as a 6 nucleotide match to the J segment corresponding to the conserved phenylalanine. The total number of nucleotides between these codons determines the length and therefore the reading frame of the CDR3 region. Processed sequence data will be deposited in the ASU secure relational database management system, which allows a WebApp front end through JasperSoft Server as well as a secure MongoDB instance allowing Ad Hoc querying. Pairing of IgH and IgIo sequences form individual cells will be conducted by a basic "if-then" algorithm, searching for complementary base pairing at the 10-mer barcode sequence stretch of each read.

REFERENCES

1. Arstila, T. P., et al., *A direct estimate of the human alphabeta T cell receptor diversity*. Science, 1999. 286 (5441): p. 958-61.
2. Bartok, I., et al., *T cell receptor CDR3 loops influence alphabeta pairing*. Mol Immunol, 2010. 47(7-8): p. 1613-8.
3. Corthay, A., K. S. Nandakumar, and R. Holmdahl, *Evaluation of the percentage of peripheral T cells with two different T cell receptor alpha-chains and of their potential role in autoimmunity*. J. Autoimmun, 2001. 16(4): p. 423-9.
4. Rani, L., et al., *Immunoglobulin heavy chain variable region gene repertoire and B-cell receptor stereotypes in Indian patients with chronic lymphocytic leukemia*. Leuk Lymphoma, 2016: p. 1-12.
5. Li, X., Dynamic changes of driver genes' mutations across clinical stages in nine cancer types. Cancer Med, 2016.
6. *New Driver Mutations Detected in NSCLC*. Cancer Discov, 2016.
7. Anoosha, P., et al., *Discrimination of driver and passenger mutations in epidermal growth factor receptor in cancer*. Mutat Res, 2015. 780: p. 24-34.
8. Bozic, I., et al., *Accumulation of driver and passenger mutations during tumor progression*. Proc Natl Acad Sci USA, 2010. 107(43): p. 18545-50.
9. Busse, C. E., et al., *Single-cell based high-throughput sequencing of full-length immunoglobulin heavy and light chain genes*. Eur J Immunol, 2014. 44(2): p. 597-603.
10. Dash, P., et al., *Paired analysis of TCRalpha and TCRbeta chains at the single-cell level in mice*. J Clin Invest, 2011. 121(1): p. 288-95.
11. DeKosky, B. J., et al., *High-throughput sequencing of the paired human immunoglobulin heavy and light chain repertoire*. Nat Biotechnol, 2013. 31(2): p. 166-9.
12. Chen, A. K., et al., *Ratiometric bimolecular beacons for the sensitive detection of RNA in single living cells*. Nucleic Acids Res, 2010. 38(14): p. e148.
13. Tyagi, S. and F. R. Kramer, *Molecular beacons: probes that fluoresce upon hybridisation*. Nat Biotechnol, 1996. 14(3): p. 303-8.
14. Mhlanga, M. M., et al., *tRNA-linked molecular beacons for imaging mRNAs in the cytoplasm of living cells*. Nucleic Acids Res, 2005. 33(6): p. 1902-12.
15. Dittmer, W. U., A. Reuter, and F. C. Simmel, *A DNA-based machine that can cyclically bind and release thrombin*. Angew Chem Int Ed Engl, 2004. 43(27): p. 3550-3.
16. Benenson, Y., et al., *An autonomous molecular computer for logical control of gene expression*. Nature, 2004. 429(6990): p. 423-9.
17. Ko, S., et al., *DNA nanotubes as combinatorial vehicles delivery*. Biomacromolecules, 2008. 9(11): p. 3039-43.
18. Chen, Y. J., et al., *DNA nanotechnology from the test tube to the cell*. Nat Nanotechnol, 2015. 10(9): p. 748-60.
19. Zhang, X., et al., *Quantitative assessment of ratiometric bimolecular beacons as a tool for imaging single engineered RNA transcripts and measuring gene expression in living cells*. Nucleic Acids Res, 2013. 41(15): p. e152.
20. Kelso, G. F., et al., *Impact on monoclonal antibody production in murine hybridoma cell cultures of adenosine receptor antagonists and phosphodiesterase inhibitors*. Bioorg Med Chem Lett, 2016. 26(2): p. 540-4.
21. Frame, K. K. and W. S. Hu, *The loss of antibody productivity in continuous culture of hybridoma cells*. Biotechnol Bioeng, 1990. 35(5): p. 469-76.
22. Franek, F. and J. Dolnikova, *Hybridoma growth and monoclonal antibody production in iron-rich protein-free medium: effect of nutrient concentration*. Cytotechnology, 1991. 7(1): p. 33-8.
23. Han, D., et al., *DNA origami with complex curvatures in three-dimensional space*. Science, 2011. 332(6027): p. 342-6.
24. Ke, Y., et al., *Scaffolded DNA origami of a DNA tetrahedron molecular container*. Nano Lett, 2009. 9(6): p. 2445-7.
25. Han, D., et al., *DNA gridiron nanostructures based four-arm junctions*. Science, 2013. 339(6126): p. 1412-5.
26. Rinker, S., et al., *Self-assembled DNA nanostructures for distance-dependent multivalent ligand-protein binding*. Nat Nanotechnol, 2008. 3(7): p. 418-22.
27. Sharma, J., et al., *Control of self-assembly DNA tubules through integration of gold nanoparticles*. Science, 2009. 323(5910): p. 112-6.
28. Ke, Y, et al., *Self-assembled water-soluble nucleic acid probe tiles for label-free RNA hybridization assays*. Science, 2008. 319(5860): p. 180-3.
29. Blattman, J. N., et al., *Evolution of the T cell repertoire during primary, memory, and recall responses to viral infection*. J Immunol, 2000. 165(11): p. 6081-90.
30. Blattman, J. N., et al., *Therapeutic use of IL-2 to enhance antiviral T-cell responses in vivo*. Nat Med, 2003. 9(5): p. 540-7.
31. Schietinger, A., et al., *Rescued tolerant CD8 T cells are preprogrammed to reestablish the tolerant state*. Science, 2012. 335(6069): p. 723-7.
32. Rothemund, P. W., *Folding DNA to create nanoscale shapes and patterns*. Nature, 2006. 440(7082): p. 297-302.
33. Mei, Q., et al., *Stability of DNA origami nanoarrays in cell lysate*. Nano Lett, 2011. 11(4): p. 1477-82.
34. Seiler, P., et al., *Enhanced virus clearance by early inducible lymphocytic choriomeningitis virus-neutralizing antibodies in immunoglobulin-transgenic mice*. J Virol, 1998. 72(3): p. 2253-8.
35. Miconnet, I., *Probing the T-cell receptor repertoire with deep sequencing*. Curr Opin HIV AIDS, 2012. 7(1): p. 64-70.

36. Venturi, V., et al., *Method for assessing the similarity between subsets of the T cell receptor repertoire.* J Immunol Methods, 2008. 329(1-2): p. 67-80.
37. Brandle, D., et al., *T cell development and repertoire of mice expressing a single T cell receptor alpha chain.* Eur J Immunol, 1995. 25(9): p. 2650-5.
38. Burns, R. P., Jr., et al., *Molecular analysis of skewed Tcra-V gene use in T-cell receptor beta-chain transgenic mice.* Immunogenetics, 1998. 47(2): p. 107-14.
39. Cabaniols, J. P., et al., *Most alpha/beta T cell receptor diversity is due to terminal deoxynucleotidyl transferase.* J Exp Med, 2001. 194(9): p. 1385-90.
40. Ewing, C., et al., *Virus-specific CD8+ T-cell responses in mice transgenic for T-cell receptor beta chain selected at random.* J Virol, 1994. 68(5): p. 3065-70.
41. Turner, S. J., S. C. Cose, and F. R. Carbone, *TCR alpha-chain usage can determine antigen-selected TCR beta-chain repertoire diversity.* J Immunol, 1996. 157(11): p. 4979-85.
42. Hayakawa, K., et al., *Isolation of high-affinity memory B cells: phycoerythrin as a probe for antigen-binding cells.* Proc Natl Acad Sci U.S.A, 1987. 84(5): p. 1379-83.
43. Venturi, V., et al., *Methods for comparing the diversity of samples of the T cell receptor repertoire.* J Immunol Methods, 2007. 321(1-2): p. 182-95.
44. Hurlbert, S. H., *The Nonconcept of Species Diversity: A Critique and Alternative Parameters.* Ecology, 1971. 52(4): p. 577.
45. Preston, F. W., *The Commonness, and Rarity, of Species.* Ecology, 1948. 29(3): p. 254-283.
46. Futschik, A. and C. Schlotterer, *The next generation of molecular markers from massively parallel sequencing of pooled DNA samples.* Genetics, 2010. 186(1): p. 207-18.
47. Johnson, P. L. and M. Slatkin, *Inference of population genetic parameters in metagenomics: a clean look at messy data.* Genome Res, 2006. 16(10): p. 1320-7.
48. Casrouge, A., et al., *Size estimate of the alpha beta TCR repertoire of naive mouse splenocytes.* J Immunol, 2000. 164(11): p. 5782-7.
49. Lynch, M., *Estimation of nucleotide diversity, disequilibrium coefficients, crud mutation rates from high-coverage genome-sequencing projects.* Mol Biol Evol, 2008. 25(11): p. 2409-19.
50. Robins, H. S., et al., *Comprehensive assessment of T-cell receptor beta-chain diversity in alphabeta T cells.* Blood, 2009. 114(19): p. 4099-107.

---

---

We claim:

1. A method for generating a barcoded bowtie DNA-nucleic acid origami nanostructure, the method comprising:
  (a) providing (i) double-stranded DNA barcode nucleic acids, wherein the barcode nucleic acid comprises a first sequence of nucleotides that can be used to distinguish and identify nucleic acids from the same cell and the first sequence of nucleotides is flanked by a priming sites complementary to one side of a single-stranded 5'-5' bowtie linker nucleic acid, the priming sites are flanked by gene specific mRNA capture sequences complementary to conserved sequences of a gene of interest; and (ii) providing a single-stranded 5'-5' bowtie linker nucleic acid comprising a central 5'-5' phosphodiester linker flanked on one side by a sequence complementary to a nucleic acid origami nanostructure and flanked on both sides of the 5'-5' phosphodiester linker by priming sites complementary to a corresponding priming site on one strand of the double-stranded DNA barcode nucleic acid;

(b) combining the double-stranded barcode nucleic acids and the 5'-5' bowtie linker nucleic acid in an oil-emulsion droplet comprising reagents for elongating a target nucleic acid;

(c) thermal cycling the oil-emulsion droplet of step (b) by (i) heating the double-stranded barcode nucleic acids and the 5'-5' bowtie linker nucleic acid sufficient to denature the double-stranded barcode nucleic acid (ii) annealing the priming sites on the single strands of the double-stranded barcode nucleic acids to complementary priming sites on the 5'-5' bowtie linker nucleic acid and (iii) elongating to produce an elongation product;

(d) extracting elongation products from the droplet;

(e) purifying ssDNA barcoded 5'-5' bowtie polynucleotides from the extracted elongation products; and (f) incorporating the purified ssDNA barcoded 5'-5' bowtie polynucleotides into a nucleic acid origami nanostructure to produce a barcoded bowtie DNA-nucleic acid origami nanostructure comprising mRNA capture sequences complementary to conserved regions of the target nucleic acid.

2. The method of claim 1, wherein incorporating comprises annealing the purified ssDNA barcoded 5'-5' bowtie polynucleotides to a nucleic acid origami nanostructure.

3. The method of claim 1, wherein the nucleic acid origami nanostructure is a DNA nanostructure.

* * * * *

SEQUENCE LISTING

```
<160> NUMBER OF SEQ ID NOS: 2

<210> SEQ ID NO 1
<211> LENGTH: 72
<212> TYPE: DNA
<213> ORGANISM: Artificial Sequence
<220> FEATURE:
<223> OTHER INFORMATION: Synthetic

<400> SEQUENCE: 1
cgagtccctt tatcgggaac gaacgtggcg agaaaggaag ggaacaaact atggacagca      60
aagacagcac ct                                                          72

<210> SEQ ID NO 2
<211> LENGTH: 111
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (50)..(61)
<223> OTHER INFORMATION: n is a, c, g, or t

<400> SEQUENCE: 2
caccgacttt gactcccaaa tcaatgtgcg gacagcaaag acagcacctn nnnnnnnnnn      60
ngctcaggga aatagccctt ggggtagcct tttgtttgtt tgcaatctct g              111
```